(12) United States Patent
Sasaki et al.

(10) Patent No.: US 11,383,106 B2
(45) Date of Patent: Jul. 12, 2022

(54) ULTRASOUND THERAPY SYSTEM

(71) Applicant: NATIONAL INSTITUTE OF ADVANCED INDUSTRIAL SCIENCE AND TECHNOLOGY, Tokyo (JP)

(72) Inventors: Akira Sasaki, Ibaraki (JP); Kiyoshi Yoshinaka, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 392 days.

(21) Appl. No.: 16/464,206

(22) PCT Filed: Nov. 24, 2017

(86) PCT No.: PCT/JP2017/042207
§ 371 (c)(1),
(2) Date: May 24, 2019

(87) PCT Pub. No.: WO2018/097245
PCT Pub. Date: May 31, 2018

(65) Prior Publication Data
US 2019/0388713 A1  Dec. 26, 2019

(30) Foreign Application Priority Data
Nov. 24, 2016  (JP) .............................. JP2016-227678

(51) Int. Cl.
*A61N 7/02* (2006.01)
*A61B 5/00* (2006.01)
(Continued)

(52) U.S. Cl.
CPC .............. *A61N 7/02* (2013.01); *A61B 5/0097* (2013.01); *A61B 5/01* (2013.01); *A61N 2007/003* (2013.01)

(58) Field of Classification Search
CPC .. A61N 7/02; A61N 2007/003; A61B 5/0097; A61B 5/01; A61B 2018/00791; A61B 8/14; A61B 17/00
See application file for complete search history.

(56) References Cited

U.S. PATENT DOCUMENTS

2009/0221900 A1* 9/2009 Ikushima ............. A61B 5/4064
600/409
2012/0265227 A1* 10/2012 Sverdlik .......... A61B 17/22012
606/169
(Continued)

FOREIGN PATENT DOCUMENTS

JP     62-284648      * 12/1987
JP     2012047751 A    3/2012
(Continued)

OTHER PUBLICATIONS

International Search Report (in English and Japanese) issued in PCT/JP2017/042207, dated Jan. 9, 2018.

*Primary Examiner* — Hien N Nguyen
(74) *Attorney, Agent, or Firm* — Harness, Dickey & Pierce, P.L.C.

(57) ABSTRACT

Provided is an ultrasound therapy system for treating a joint by providing a focused ultrasound wave to a bone surface as an affected part, and which has a temperature monitoring function for controlling irradiation intensity. The ultrasound therapy system includes a focused ultrasound wave providing unit provided on skin and configured to radiate the focused ultrasound wave to the affected part, and a temperature detecting unit configured to measure a temperature of the affected part. The temperature detecting unit includes an electromagnetic wave measuring unit configured to measure intensity of an electromagnetic wave radiated from the bone surface, and an analyzing unit configured to analyze change of the electromagnetic wave of the electromagnetic wave (Continued)

measuring unit to provide the temperature of the affected part. The analyzing unit provides the temperature of the affected part from electromagnetic change between a pair of reference waves for electromagnetic change which correspond to a pair of an emitted wave of the focused ultrasound wave provided from the focused ultrasound wave providing unit and a reflected wave from the bone surface and which are measured at the electromagnetic wave measuring unit with a time delay.

10 Claims, 3 Drawing Sheets

(51) Int. Cl.
*A61B 5/01* (2006.01)
*A61N 7/00* (2006.01)

(56) References Cited

U.S. PATENT DOCUMENTS

2013/0046178 A1 2/2013 Cho et al.
2017/0209708 A1* 7/2017 Schwarz .............. A61H 23/008

FOREIGN PATENT DOCUMENTS

JP 2013043082 A 3/2013
JP 2015217247 A 12/2015

* cited by examiner (a)

(b)

ULTRASOUND THERAPY SYSTEM

CROSS-REFERENCE TO RELATED APPLICATIONS

This application is the U.S. National Phase Application under 35 U.S.C. 371 of International Application No. PCT/JP2017/042207, filed on Nov. 24, 2017, which claims the benefit of priority from Japanese Patent Application No. 2016-227678, filed on Nov. 24, 2016. The entire disclosures of these applications are incorporated herein by reference in their entirety.

TECHNICAL FIELD

The present invention relates to an ultrasound therapy system for performing treatment by providing a focused ultrasound wave to an affected part, and, particularly, relates to an ultrasound therapy system having a temperature monitoring function for controlling irradiation intensity of a focused ultrasound wave on a bone surface as an affected part.

Focused ultrasound surgery (FUS) which enables treatment of an affected part in a non-invasive manner using a high-intensity focused ultrasound (HIFU) is known.

For example, PTL 1 discloses a focused ultrasound therapy system in which the HIFU is radiated throughout a treatment target region (target) by sequentially moving a position of a focal point which is an irradiation position of the HIFU. Here, an applicator is used in which an imaging probe including an imaging oscillator for capturing an ultrasound image is incorporated into a multi-element transducer in which a plurality of treatment oscillators are arranged on a semispherical concave surface in a dispersed manner. Typically, while an incident angle of a focused ultrasound wave with respect to a body surface differs depending on a position of the applicator or a shape of the body surface to which the applicator is to be pressed, because the incident angle can be calculated from an ultrasound image captured by an imaging probe and can be fed back and controlled, energy transmission efficiency to inside of a living body and a focal point can be changed.

As described above, to control irradiation of an ultrasound wave inside a body, because an irradiated position cannot be directly visually checked, some kinds of monitoring means are required.

For example, PTL 2 discloses a method for monitoring a temperature by utilizing an ultrasound wave for treatment in a treatment apparatus for removing and treating a tumor by radiating the HIFU while focusing on a tumor site to be treated to locally destroy tumor tissues or cause necrosis of the tumor tissues. PTL 2 describes that a CBE (Change in Backscattered Energy) method, an ES (Echo-Shift) method, or the like, are known as a temperature detection method for monitoring a temperature by utilizing an ultrasound wave, and temperature monitoring with high accuracy is provided by combination of these methods.

PTL 1 describes that, because noise occurs in an image if capturing of an ultrasound image and irradiation of an ultrasound wave are performed at the same time, the transducer which radiates an ultrasound wave and the imaging probe which captures an ultrasound image are caused to alternately operate to acquire a clear diagnostic image with no noise. Therefore, monitoring means other than an ultrasound wave is considered.

For example, PTL 3 discloses a method of detecting change of a portion such as inside of a human body, which cannot be visually checked, by ultrasound irradiation by utilizing a fact that change of characteristic values of charged particles at a portion irradiated with an ultrasound wave can be measured from change of intensity of an electromagnetic wave radiated from the portion (a characteristic measurement method of an object using an acoustically induced electromagnetic wave). Here, PTL 3 describes that an active portion of neurons of a brain, an active portion of muscle tissues, or the like, can be detected.

CITATION LIST

Patent Literature

PTL 1: Japanese Patent Laid-Open No. 2015-217247
PTL 2: Japanese Patent Laid-Open No. 2013-43082
PTL 3: Japanese Patent Laid-Open No. 2012-47751

SUMMARY OF INVENTION

Technical Problem

In accordance with increase in population of elderly people, the number of patients of arthrosis rapidly increases, and, concerning painful arthrosis which prevents a patient from performing daily activities, particularly, arthrosis of the knee, treatment and pain relief (bone pain relief) through cauterization of an affected part using the HIFU are expected as a method which is less stressful on a human body. For example, it becomes possible to relieve pain of a bone by cauterizing a surface of a cortical bone (compact bone) using the HIFU to destroy neural tissues between periostea and the cortical bone. Furthermore, it is possible to perform treatment by thermally cauterizing a bone surface by radiating an ultrasound wave on the cortical bone through skin.

While monitoring for controlling irradiation of the HIFU is also desired here, there are a lot of problems in terms of operability, cost, or the like, in introduction of a large-scale monitoring system which is to be combined with a magnetic resonance imaging (MRI) apparatus and, thus, a simpler method is desired.

The present invention has been made in view of the circumstances as described above, and an object of the present invention is to provide an ultrasound therapy system which is a treatment system that relieves pain or treats a bone and a joint by providing a focused ultrasound wave on a bone surface as an affected part, and which has a monitoring function for controlling irradiation intensity.

Solution to Problem

The present inventor has considered that it is only necessary to perform at least monitoring of change of a temperature of an affected part in treatment and pain relief (bone pain relief) by cauterization of the affected part of arthrosis such as arthrosis of the knee using HIFU. As a result of intensive studies, the present inventor has found that a temperature can be monitored from change of an electromagnetic wave from the affected part, and this electromagnetic change is caused also by denaturation by cauterization of the affected part.

That is, an ultrasound therapy system according to the present invention for performing treatment by providing a focused ultrasound wave to an affected part, is an ultrasound therapy system for treating the affected part by providing a focused ultrasound wave to a bone surface as the affected part from a surface of skin in the vicinity of the bone surface, including a focused ultrasound wave providing unit provided on the skin and configured to radiate the focused ultrasound wave to the affected part, and a temperature measuring unit configured to measure a temperature of the affected part, the temperature measuring unit including an electromagnetic wave measuring unit configured to measure intensity of an electromagnetic wave radiated from a radiating unit of the focused ultrasound wave, and an analyzing unit configured to analyze change of the electromagnetic wave of the electromagnetic wave measuring unit to provide the temperature of the affected part, and the analyzing unit providing the temperature of the affected part from electromagnetic change between a pair of reference waves for electromagnetic change which correspond to a pair of an emitted wave of the focused ultrasound wave provided from the focused ultrasound wave providing unit and a reflected wave from the bone surface and which are measured at the electromagnetic wave measuring unit with a time delay.

According to this invention, in treatment performed by providing the focused ultrasound wave to the bone surface as an affected part from the surface of skin in the vicinity of the bone surface, it is possible to monitor the temperature of the affected part from electromagnetic change, for example, change of intensity of the electromagnetic wave without using large-scale measuring means, so that it is possible to accurately control irradiation intensity of the focused ultrasound wave to the affected part.

In the above-described invention, the focused ultrasound wave providing unit may be able to provide the emitted wave as a burst wave. According to this invention, because the reference waves can be made clear, it is possible to accurately separate electromagnetic change between the reference waves, so that it is possible to monitor a temperature with higher accuracy.

In the above-described invention, the focused ultrasound wave providing unit may provide a continuous wave for cauterizing the affected part subsequent to the burst wave. According to this invention, because the reference waves can be made clear, it is possible to accurately separate electromagnetic change between the reference waves, so that it is possible to monitor a temperature with higher accuracy and it is possible to widely control a degree of cauterization of the affected part.

In the above-described invention, the analyzing unit may obtain the electromagnetic change and a temperature in association with each other in advance, and may provide the temperature of the affected part from the electromagnetic change provided from the electromagnetic wave measuring unit. Furthermore, the analyzing unit may associate the electromagnetic change with a known denaturation temperature of a bone tissue in advance, and may provide the denaturation temperature as the temperature of the affected part. According to this invention, it is possible to perform temperature monitoring of the affected part, which is particularly appropriate for treatment of a cortical bone and a joint from change of intensity of the electromagnetic wave in denaturation from a collagen tissue which is a bone tissue to gelatinous texture, and because at least completion of denaturation appears in the electromagnetic change, completion of cauterization can be clearly obtained, so that it is possible to accurately control irradiation intensity of the focused ultrasound wave to the affected part.

In the above-described invention, the denaturation temperature may depend on denaturation of a collagen tissue which is part of the bone tissue. According to this invention, it is possible to monitor a temperature, particularly, in a temperature range between approximately 50 and 60° C. which is a denaturation temperature of the bone.

In the above-described invention, the focused ultrasound wave providing unit may radiate the focused ultrasound wave while controlling the focused ultrasound wave in accordance with the temperature of the affected part. According to this invention, it is possible to perform accurate control of irradiation intensity of the focused ultrasound wave in which a state of the affected part is reflected.

In the above-described invention, the electromagnetic wave measuring unit may include a coil, and the focused ultrasound wave providing unit may include a transducer unit which provides the focused ultrasound wave to the affected part while allowing the focused ultrasound wave to pass through inside of the coil. According to this invention, it is possible to monitor a temperature of the affected part for controlling irradiation intensity of the focused ultrasound wave to the affected part without providing large-scale measuring means in the ultrasound therapy system.

In the above-described invention, the coil may be configured to be able to be pressed against a surface of skin in the vicinity of the affected part. Furthermore, the coil may be disposed so as to allow a beam axial line of the focused ultrasound wave to pass through inside. According to this invention, even if intensity of the electromagnetic wave in denaturation from a collagen tissue which is a bone tissue to gelatinous texture is extremely small, because it is possible to efficiently receive an electromagnetic wave to be generated, it is possible to accurately separate and measure change of the reference electromagnetic waves and change of a measured electromagnetic wave, so that it is possible to monitor a temperature with higher accuracy.

DESCRIPTION OF EMBODIMENTS

Before an ultrasound therapy system having a temperature monitoring function will be described in detail as an example of the present invention, principle will be described first.

It is known that bone tissues (such as a cortical bone and a cartilage) generate an electromagnetic wave by irradiation of an ultrasound wave. Meanwhile, a cortical bone among the bone tissues is formed with osten which is collagenous tissues, and, in a case of human, spiral collagenous tissues change to gelatinous texture (glue) at 42° C. which is a denaturation start temperature, and completes its denaturation to the gelatinous texture around 60° C. That is, in accordance with increase in a temperature at a focal point of irradiation of an ultrasound wave, generation intensity of an electromagnetic wave from the bone tissues continuously decreases as the collagen tissues decrease, and crystalline texture dissolves around 60° C. and generation of an electromagnetic wave also disappears. By utilizing such relationship between increase in a temperature and generation intensity of an electromagnetic wave, it is possible to measure intensity of the electromagnetic wave to measure a temperature at a focal point (irradiated part) of irradiation of an ultrasound wave, so that it is possible to clearly measure at least completion of denaturation to gelatinous texture. That is, in ultrasound therapy, it is possible to increase a temperature of the affected part to a necessary certain temperature without increasing the temperature of the affected part higher than necessary.

Subsequently, the ultrasound therapy system having the temperature monitoring function will be described as an example of the present invention while referring to FIG. 1 to FIG. 3.

Figure 1:
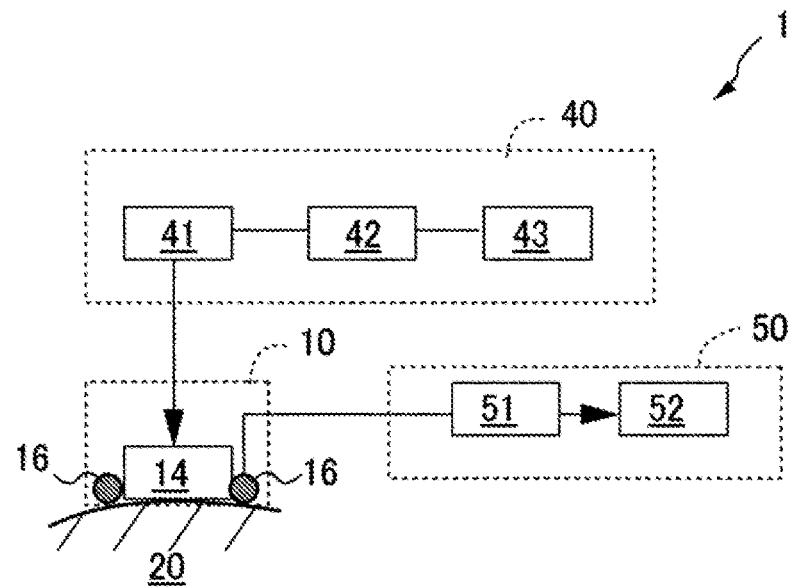
FIG. 1 is a block diagram illustrating an ultrasound therapy system according to the present invention.

As illustrated in FIG. 1, the ultrasound therapy system 1 includes a focused ultrasound wave providing unit including a transducer 14 provided inside an ultrasound applicator 10 for radiating a focused ultrasound wave toward the affected part 20, and an input control unit 40 for controlling the focused ultrasound wave output from this transducer 14, and a temperature measuring unit including a sensor coil 16 which detects an electromagnetic wave from the affected part 20, and a temperature detecting unit 50 which processes signals from the sensor coil 16. Here, the sensor coil 16 is provided inside or outside the applicator 10.

Figure 2:
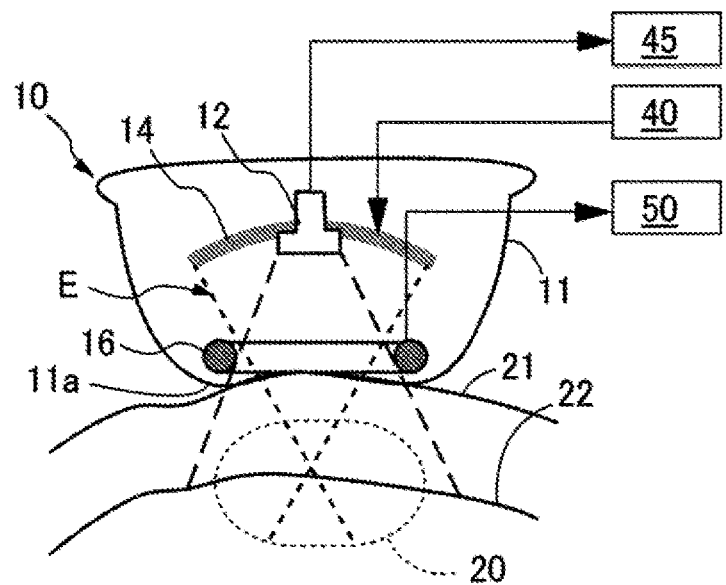
FIG. 2 is a diagram illustrating an applicator to be used in the present invention.

Referring to FIG. 2 which is a detail view of the applicator 10 in FIG. 1, the applicator 10 is a water bag in which water is kept inside, a semispherical transducer 14 formed with piezo elements is accommodated inside a case 11 of the applicator 10, a convex portion 11a of the case 11 is brought into close contact with skin 21, and the applicator 10 is used to provide a focused ultrasound wave E to the affected part 20 in the vicinity of a bone surface 22.

Note that publicly known various kinds of control forms can be used as the input control unit 40 for controlling the focused ultrasound wave E output from the transducer 14 within the applicator 10. For example, the input control unit 40 includes a drive circuit 41 of the transducer 14, an input unit 43 which inputs a desired output waveform, and a control circuit 42 which sends out a signal to the drive circuit 41 in accordance with input by the input unit 43.

Furthermore, a diagnosis ultrasound probe 12 may be provided as appropriate to enable an image inside a living body around the affected part 20 to be obtained by an ultrasound diagnosis unit 45.

The temperature detecting unit 50 includes a sensor coil 16 which detects an electromagnetic wave from the affected part 20, a conversion circuit unit 51 which performs A/D conversion on the output voltage to obtain a signal waveform, and a signal processing determining unit 52 which performs filtering processing on the signal waveform to, as will be described later, convert the signal into a temperature.

Furthermore, the sensor coil 16 is provided inside or outside the case 11 of the applicator 10 so as to allow the focused ultrasound wave from the transducer 14 to pass through inside. Typically, the sensor coil 16 is provided at the convex portion 11a of the case 11 of the applicator 10, and is configured to be able to be pressed against skin 21 in the vicinity of the affected part 20. By this means, it is possible to locate the sensor coil 16 at a position in the vicinity of the affected part which is an irradiation portion of the focused ultrasound wave, and provide a principal surface of the sensor coil 16 vertically in a traveling direction (axial line direction) of the focused ultrasound wave, so that it is possible to realize reliable capturing of an electromagnetic wave by the sensor coil 16 which will be described later.

Figure 3:
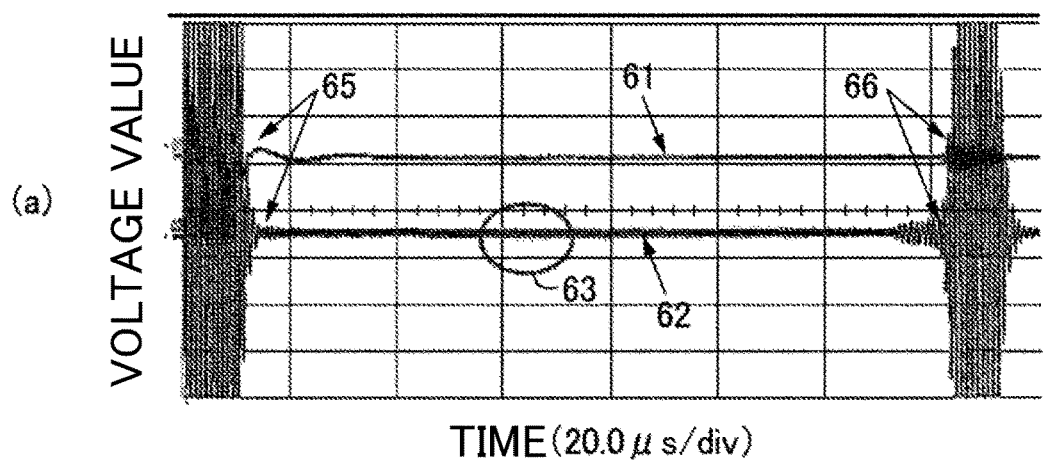
FIG. 3 is a chart illustrating an example of a voltage signal to be measured at the applicator in the present invention.
Figure 3:
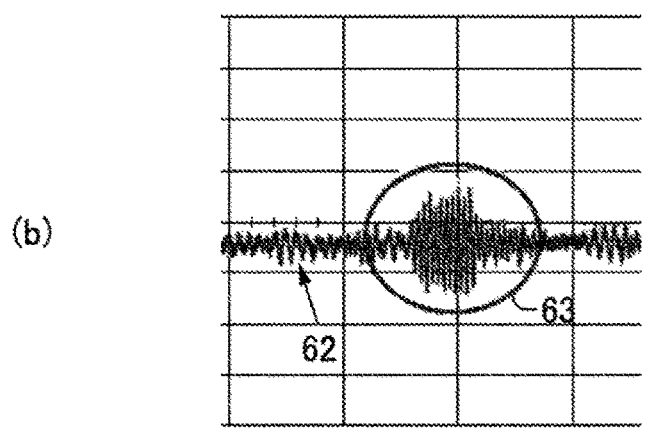

FIG. 3 illustrates an example of a graph of voltage change measured at the sensor coil 16 when the affected part 20 is irradiated with the focused ultrasound wave from the transducer 14. Note that FIG. 3(b) is an enlarged view of the waveform in FIG. 3(a). Here, a waveform 61 indicates voltage change provided from the input control unit 40 to the transducer 14, and a waveform 62 indicates voltage change based on the electromagnetic wave measured at the sensor coil 16. Peaks 65 of the waveforms 61 and 62 result from an emitted wave of the focused ultrasound wave, and peaks 66 result from a reflected wave which is reflected at the affected part (irradiated part), and the emitted wave and the reflected wave are measured with a time delay. Note that, even if the peaks 65 and 66 of the waveform 62 are not clearly observed, it is possible to capture the peaks 65 and 66 of the waveform 62 from time of the peaks 65 and 66 in the waveform 61.

In Particular, as illustrated in FIG. 3(b), in the waveform 62, small change 63 of an electromagnetic wave (change in a measured electromagnetic wave) is observed between the waveform peak 65 and the waveform peak 66 which are made reference waves in accordance with change of the electromagnetic wave, and in the vicinity of an intermediate portion thereof on a time axis. That is, when the emitted wave and the reflected wave reciprocate on a path, the focused ultrasound wave reaches the affected part (irradiated part) at a substantially intermediate time position of time corresponding to the waveform peak 65 and time corresponding to the waveform peak 66 on a time axis. Because speed of the electromagnetic wave generated at this time is faster than speed of the ultrasound wave, the electromagnetic wave can be immediately captured with the sensor coil 16 as change 63 of the electromagnetic wave. Because this change of the electromagnetic wave has electromagnetic wave intensity in accordance with the state of the affected part (irradiated part), and, particularly, decrease of the collagen tissues is reflected, temperature information by denaturation of collagen can be obtained.

In this manner, first, time positions corresponding to the waveform peak 65 and the waveform peak 66 are determined on a time axis of the waveform 62, and the reference waves are separated from a base line at the intermediate position of the time positions. By this means, it is possible to separate small change (change of a measured electromagnetic wave) 63 of the electromagnetic wave, and measure a temperature of the affected part (irradiated part) by amplifying and observing the change.

Here, by a burst wave-like wave which is intermittently oscillated being input to the transducer 14, the waveform peaks 65 and 66 can be obtained more clearly as change of the reference electromagnetic waves. Furthermore, the burst wave and a continuous wave may be repeatedly provided for interleaving in a discontinuous manner. By the continuous wave being provided subsequent to the burst wave, while the affected part is cauterized by the continuous wave, a temperature is measured by the burst wave, and, thereby control of cauterization can be separated, so that it is possible to increase controllability of treatment of the affected part.

As described above, if denaturation temperatures of bone tissues of the affected part 20 are, for example, 42° C. and 60° C., at least electromagnetic change with respect to these temperatures is clearly measured. Furthermore, by a calibration curve of a temperature with respect to electromagnetic change being obtained, it is also possible to continuously monitor a temperature between the denaturation temperatures, that is, the temperature of the affected part 20. Such temperature monitoring from change of intensity of the electromagnetic wave corresponding to denaturation from the collagen tissues which are bone tissues to gelatinous texture is appropriate for treatment based on such denaturation, particularly, treatment for pain relief of a bone and a joint.

According to the system and the method described above, it is possible to radiate a focused ultrasound wave while enabling temperature monitoring on matter which generates an electromagnetic wave by irradiation of a focused ultrasound wave, such as a cartilage and a tendon as well as a cortical bone. For example, it becomes possible to perform monitoring which thermally destructs nerves located between bones and periostea, it is possible to perform non-invasive pain relief treatment under temperature management in pain relief of a bone metastatic cancer and local bone treatment.

Note that, while an example has been described where the sensor coil 16 is provided so as to correspond to one transducer 14, a temperature can be measured in a similar manner by a plurality of sensor coils being incorporated into a multi-element transducer-type applicator which cauterizes one location with a plurality of transducers.

Example

An example will be described where the burst wave intermittently oscillated at 1 MHz is radiated to a bone chip of femur (cortical bone) of a pig as the focused ultrasound wave and a temperature is measured through measurement of an electromagnetic wave by the ultrasound therapy system 1 described above. Note that the sensor coil 16 is obtained by winding a wire at a size which does not inhibit progression of the focused ultrasound wave which passes through inside.

First, a preliminary examination regarding intensity of an electromagnetic wave measured with respect to change of a distance between the sensor coil 16 and the affected part (bone chip) was performed.

Figure 4:
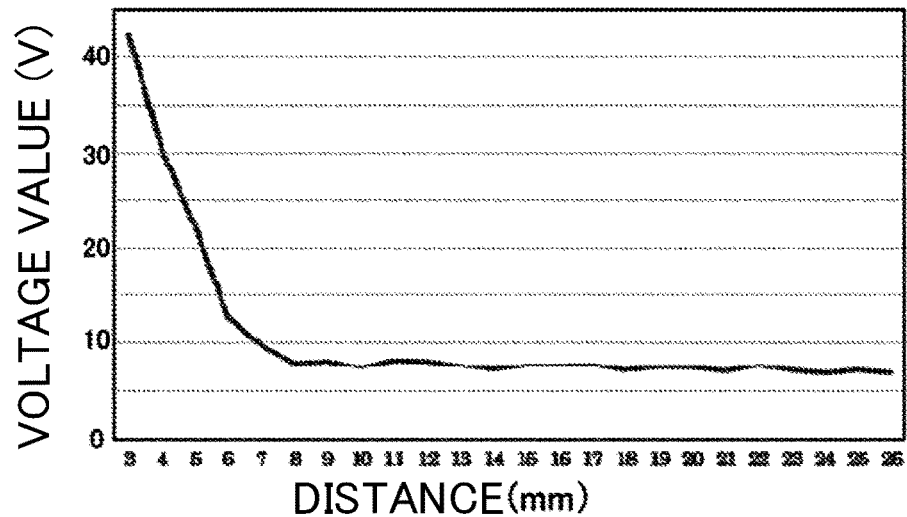
FIG. 4 is a graph illustrating change of a voltage value to be measured with respect to a distance between an affected part and a sensor coil.

As illustrated in FIG. 4, it was found that a voltage output from the sensor coil 16 rapidly decreased as a result of increase in the distance between the sensor coil 16 and the bone chip, and intensity of the electromagnetic wave largely decreased. That is, the sensor coil 16 is preferably located at a position close to the affected part, and, at least preferably located within approximately several millimeters from the affected part.

Figure 5:
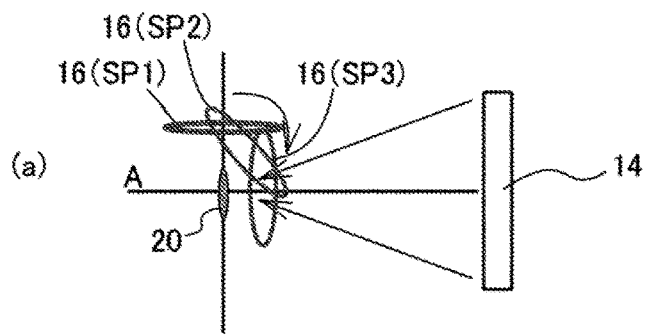
FIG. 5 is a graph illustrating relationship between an inclination angle of the sensor coil with respect to an axial line of a focused ultrasound wave and change of an electromagnetic wave to be measured.
Figure 5:
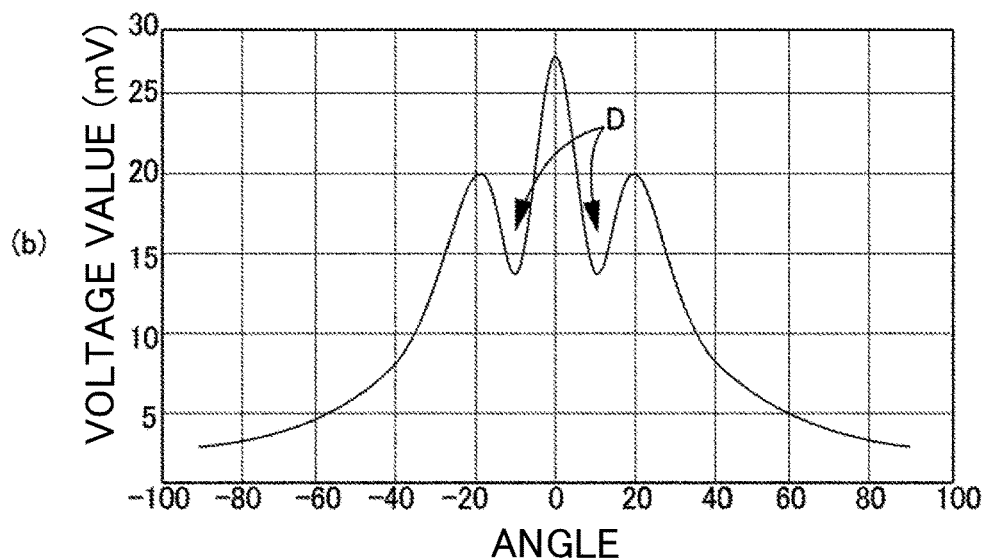

FIG. 5 illustrates a graph of change of the voltage output from the sensor coil 16 when an ultrasound beam from the transducer 14 is radiated to the affected part 20 and an angle of the sensor coil 16 with respect to an axial line A of the ultrasound beam is changed. A ratio of detection sensitivity of the electromagnetic wave, that is, a voltage value becomes a maximum when a principle surface of the sensor coil 16 is disposed perpendicular to the axial line A of the ultrasound beam (see SP3 in FIG. 5(*a*)). If the principle surface of the sensor coil 16 is rotated (see SP2 in FIG. 5(*a*)), because the winding wire of the sensor coil 16 temporarily crosses the axial line A of the ultrasound beam, while the voltage value drops once (see D in FIG. 5(*b*)), the voltage value continuously decreases until the principle surface of the sensor coil 16 becomes parallel (see SP1 in FIG. 5(*a*)). That is, to improve detection sensitivity of the electromagnetic wave, the sensor coil 16 is preferably disposed so that the principle surface is located in a beam axial line direction A of the focused ultrasound waves.

Figure 6:
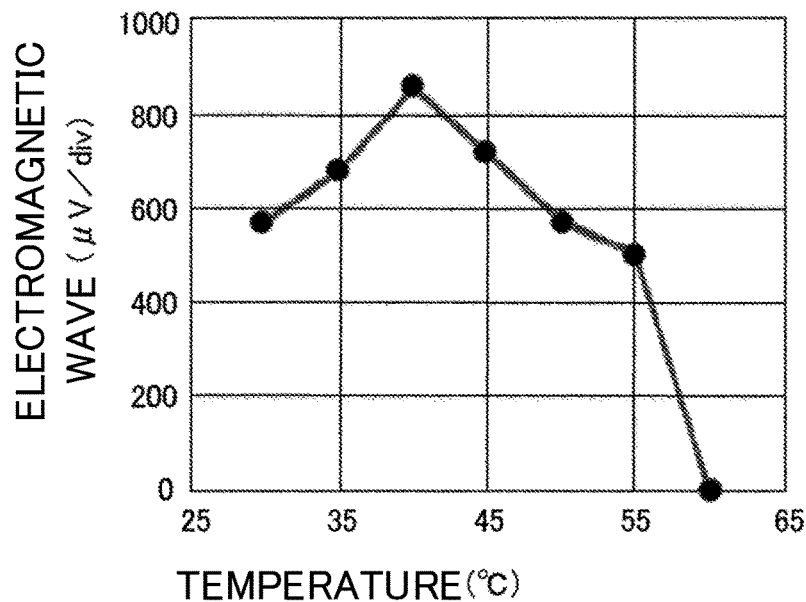
FIG. 6 is a graph illustrating relationship between change of an electromagnetic wave and a temperature.

Then, FIG. 6 illustrates a result of examination of relationship between the intensity of the electromagnetic wave and the temperature of the affected part.

Here, while the intensity of the electromagnetic wave rapidly decreased from 55° C. to 60° C., this is change of intensity of the electromagnetic wave by denaturation of collagen tissues, and the intensity became zero at 60° C. It can be detected from this change of intensity of the electromagnetic wave that cauterization of the affected part completely progresses, and, inversely, it can be determined that the temperature is 60° C. from characteristics of the collagen tissues. By obtaining a detection line of such a temperature with respect to the intensity of the electromagnetic wave, for example, when 500 µV/div is observed, it can be determined that the temperature of the affected part is approximately 55° C., and, when 700 µV/div is observed, it can be determined that the temperature is approximately 45° C.

While a typical example according to the present invention and modified examples based on the example have been described above, the present invention is not necessarily limited to these. A person skilled in the art would find various alternative examples without deviating from the appended claims.

REFERENCE SIGNS LIST

1 ultrasound therapy system
10 applicator
11 case
14 transducer
16 sensor coil
20 affected part
40 input control unit
41 drive circuit
43 input unit
45 ultrasound diagnosis unit
50 temperature detecting unit
51 conversion circuit unit
52 signal processing determining unit

The invention claimed is:

1. An ultrasound therapy system for treating an affected part by providing a focused ultrasound wave to a bone surface as the affected part from a surface of skin in a vicinity of the bone surface, comprising:
  a focused ultrasound wave providing unit provided on the skin and configured to radiate the focused ultrasound wave to the affected part;
  a temperature measuring unit configured to measure a temperature of the affected part, and
  a water bag in which water is kept inside;
  wherein the temperature measuring unit including:
  an electromagnetic wave measuring unit configured to measure intensity of an electromagnetic wave radiated from a radiating unit of the focused ultrasound wave; and
  an analyzing unit configured to analyze change of the electromagnetic wave of the electromagnetic wave measuring unit to provide the temperature of the affected part, and
  the analyzing unit provides the temperature of the affected part from electromagnetic change between a pair of reference waves for electromagnetic change which correspond to a pair of an emitted wave of the focused ultrasound wave provided from the focused ultrasound wave providing unit and a reflected wave from the bone surface and which are measured at the electromagnetic wave measuring unit with a time delay, wherein the electromagnetic wave measuring unit includes a coil, and the focused ultrasound wave providing unit includes a transducer unit which provides the focused ultrasound wave to the affected part while allowing the focused ultrasound wave to pass through inside of the coil, and wherein the water bag accommodates the coil and the transducer unit.

2. The ultrasound therapy system according to claim 1, wherein the focused ultrasound wave providing unit provides the emitted wave as a burst wave.

3. The ultrasound therapy system according to claim 2, wherein the focused ultrasound wave providing unit provides a continuous wave for cauterizing the affected part subsequent to the burst wave.

4. The ultrasound therapy system according to claim 1, wherein the analyzing unit obtains the electromagnetic change and a temperature in association with each other in advance, and provides the temperature of the affected part from the electromagnetic change provided from the electromagnetic wave measuring unit.

5. The ultrasound therapy system according to claim 4, wherein the analyzing unit associates the electromagnetic change with a known denaturation temperature of a bone tissue in advance and provides the denaturation temperature as the temperature of the affected part.

6. The ultrasound therapy system according to claim 5, wherein the denaturation temperature depends on denaturation of a collagen tissue which is part of the bone tissue.

7. The ultrasound therapy system according to claim 6, wherein the focused ultrasound wave providing unit radiates the focused ultrasound wave while controlling the focused ultrasound wave in accordance with the temperature of the affected part.

8. The ultrasound therapy system according to claim 1, wherein the coil is configured to be able to be pressed against a surface of skin in a vicinity of the affected part.

9. The ultrasound therapy system according to claim 8, wherein the coil is disposed so as to allow a beam axial line of the focused ultrasound wave to pass through inside.

10. The ultrasound therapy system according to claim 1, wherein the coil is located between the transducer unit and the affected part.

* * * * *